(12) United States Patent
Rhee et al.

(10) Patent No.: US 12,064,119 B2
(45) Date of Patent: Aug. 20, 2024

(54) ELECTROLYTIC DETACHMENT FOR IMPLANTABLE DEVICES

(71) Applicant: Covidien LP, Mansfield, MA (US)

(72) Inventors: Richard Rhee, Anaheim Hills, CA (US); Madhur Kadam, Lake Forest, CA (US); Vincent Divino, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 974 days.

(21) Appl. No.: 16/948,588

(22) Filed: Sep. 24, 2020

(65) Prior Publication Data

US 2021/0000477 A1  Jan. 7, 2021

Related U.S. Application Data

(63) Continuation of application No. 15/616,981, filed on Jun. 8, 2017, now Pat. No. 10,828,039.

(60) Provisional application No. 62/354,968, filed on Jun. 27, 2016.

(51) Int. Cl.
*A61B 17/12* (2006.01)
*A61B 17/00* (2006.01)

(52) U.S. Cl.
CPC .. *A61B 17/12113* (2013.01); *A61B 17/12099* (2013.01); *A61B 17/1214* (2013.01); *A61B 17/12172* (2013.01); *A61B 2017/00526* (2013.01); *A61B 2017/12063* (2013.01)

(58) Field of Classification Search
CPC ........ A61B 17/12113; A61B 17/12172; A61B 17/12168; A61B 17/12099; A61B 17/12109; A61B 2017/12063; A61B 2017/1205; A61B 2017/12054; A61B 17/12022
See application file for complete search history.

(56) References Cited

U.S. PATENT DOCUMENTS

| | | |
|---|---|---|
| 5,108,407 A | 4/1992 | Geremia et al. |
| 5,122,136 A | 6/1992 | Guglielmi et al. |
| 5,250,071 A | 10/1993 | Palermo |

(Continued)

FOREIGN PATENT DOCUMENTS

| | | |
|---|---|---|
| CN | 101835430 A | 9/2010 |
| DE | 4445715 A1 | 6/1996 |

(Continued)

OTHER PUBLICATIONS

International Search Report and Written Opinion dated Aug. 4, 2017, International Patent Application No. PCT/US2017/036699, 16 pages.

*Primary Examiner* — Katherine H Schwiker
(74) *Attorney, Agent, or Firm* — Fortem IP LLP

(57) ABSTRACT

Delivery and detachment of an implant can be enhanced by a retraction mechanism to secure portions of a delivery wire within an interior space of the implant. A delivery system can include an implant having a proximal end portion. A delivery wire can include (i) a detachment zone proximal to the proximal end portion and (ii) a distal region distal to the proximal end portion. An expansion member can be located between the proximal end portion and the distal region of the delivery wire. The expansion member can be biased to move the distal region of the delivery wire distally away from the proximal end portion when severed at the detachment zone.

17 Claims, 6 Drawing Sheets

(56) References Cited

U.S. PATENT DOCUMENTS

| | | |
|---|---|---|
| 5,354,295 A | 10/1994 | Guglielmi et al. |
| 5,370,653 A | 12/1994 | Cragg |
| 5,423,829 A | 6/1995 | Pham et al. |
| 5,509,411 A | 4/1996 | Littmann et al. |
| 5,522,836 A | 6/1996 | Palermo |
| 5,540,680 A | 7/1996 | Guglielmi et al. |
| 5,624,449 A | 4/1997 | Pham et al. |
| 5,658,308 A | 8/1997 | Snyder |
| 5,669,931 A | 9/1997 | Kupiecki et al. |
| 5,690,667 A | 11/1997 | Gia |
| 5,733,329 A | 3/1998 | Wallace et al. |
| 5,743,905 A | 4/1998 | Eder et al. |
| 5,749,894 A | 5/1998 | Engelson |
| 5,766,629 A | 6/1998 | Cho et al. |
| 5,800,455 A | 9/1998 | Palermo et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,128 A | 4/1999 | Gia et al. |
| 5,895,385 A | 4/1999 | Guglielmi et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,928,226 A | 7/1999 | Guglielmi et al. |
| 5,935,145 A | 8/1999 | Villar et al. |
| 5,941,888 A | 8/1999 | Wallace et al. |
| 5,944,114 A | 8/1999 | Farley |
| 5,947,962 A | 9/1999 | Guglielmi et al. |
| 5,947,963 A | 9/1999 | Guglielmi |
| 5,951,599 A | 9/1999 | McCrory |
| 5,964,797 A | 10/1999 | Ho |
| 5,976,126 A | 11/1999 | Guglielmi |
| 5,984,929 A | 11/1999 | Bashiri et al. |
| 6,010,498 A | 1/2000 | Guglielmi |
| 6,013,084 A | 1/2000 | Ken et al. |
| 6,059,779 A | 5/2000 | Mills |
| 6,063,070 A | 5/2000 | Eder |
| 6,063,104 A | 5/2000 | Villar et al. |
| 6,066,133 A | 5/2000 | Guglielmi et al. |
| 6,077,260 A | 6/2000 | Wheelock et al. |
| 6,083,220 A | 7/2000 | Guglielmi et al. |
| 6,123,714 A | 9/2000 | Gia et al. |
| 6,136,015 A | 10/2000 | Kurz et al. |
| 6,146,373 A | 11/2000 | Cragg et al. |
| 6,156,061 A | 12/2000 | Wallace et al. |
| 6,165,178 A | 12/2000 | Bashiri et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,193,728 B1 | 2/2001 | Ken et al. |
| 6,238,403 B1 | 5/2001 | Greene et al. |
| 6,241,691 B1 | 6/2001 | Ferrera et al. |
| 6,280,457 B1 | 8/2001 | Wallace et al. |
| 6,296,622 B1 | 10/2001 | Kurz et al. |
| 6,299,619 B1 | 10/2001 | Greene et al. |
| 6,306,153 B1 | 10/2001 | Kurz et al. |
| 6,309,367 B1 | 10/2001 | Boock |
| 6,371,972 B1 | 4/2002 | Wallace et al. |
| 6,409,721 B1 | 6/2002 | Wheelock et al. |
| 6,416,373 B1 | 7/2002 | Kolb et al. |
| 6,425,893 B1 | 7/2002 | Guglielmi |
| 6,425,914 B1 | 7/2002 | Wallace et al. |
| 6,468,266 B1 | 10/2002 | Bashiri et al. |
| 6,468,301 B1 | 10/2002 | Amplatz et al. |
| 6,478,773 B1 | 11/2002 | Gandhi et al. |
| 6,485,524 B2 | 11/2002 | Strecker |
| 6,486,266 B2 | 11/2002 | Amano et al. |
| 6,511,468 B1 | 1/2003 | Cragg et al. |
| 6,533,801 B2 | 3/2003 | Wallace et al. |
| 6,558,367 B1 | 5/2003 | Cragg et al. |
| 6,589,230 B2 | 7/2003 | Gia et al. |
| 6,589,236 B2 | 7/2003 | Wheelock et al. |
| 6,602,261 B2 | 8/2003 | Greene et al. |
| 6,605,101 B1 | 8/2003 | Schaefer et al. |
| 6,620,152 B2 | 9/2003 | Guglielmi |
| 6,623,493 B2 | 9/2003 | Wallace et al. |
| 6,723,112 B2 | 4/2004 | Ho et al. |
| 6,743,251 B1 | 6/2004 | Eder |
| 6,835,185 B2 | 12/2004 | Ramzipoor et al. |
| 6,878,384 B2 | 4/2005 | Cruise et al. |
| 6,905,503 B2 | 6/2005 | Gifford et al. |
| 6,936,055 B1 | 8/2005 | Ken et al. |
| 6,953,473 B2 | 10/2005 | Porter |
| 6,964,657 B2 | 11/2005 | Cragg et al. |
| 6,966,892 B2 | 11/2005 | Gandhi et al. |
| 7,014,645 B2 | 3/2006 | Greene et al. |
| 7,083,567 B2 | 8/2006 | Mawad |
| 7,128,736 B1 | 10/2006 | Abrams et al. |
| 7,166,122 B2 | 1/2007 | Aganon et al. |
| 7,169,172 B2 | 1/2007 | Levine et al. |
| 7,198,613 B2 | 4/2007 | Gandhi et al. |
| 7,229,461 B2 | 6/2007 | Chin et al. |
| 7,238,194 B2 | 7/2007 | Monstadt et al. |
| 7,255,707 B2 | 8/2007 | Ramzipoor et al. |
| 7,300,458 B2 | 11/2007 | Henkes et al. |
| 7,323,000 B2 | 1/2008 | Monstdt et al. |
| 7,331,974 B2 | 2/2008 | Schaefer et al. |
| 7,485,122 B2 | 2/2009 | Teoh |
| 7,524,322 B2 | 4/2009 | Monstadt et al. |
| 7,601,160 B2 | 10/2009 | Richter |
| 7,608,089 B2 | 10/2009 | Wallace et al. |
| RE41,029 E | 12/2009 | Guglielmi et al. |
| 7,651,513 B2 | 1/2010 | Teoh et al. |
| 7,695,484 B2 | 4/2010 | Wallace et al. |
| 7,879,064 B2 | 2/2011 | Monstadt et al. |
| 7,896,899 B2 | 3/2011 | Patterson et al. |
| 7,938,845 B2 | 5/2011 | Aganon et al. |
| RE42,625 E | 8/2011 | Guglielmi |
| 8,002,789 B2 | 8/2011 | Ramzipoor et al. |
| RE42,756 E | 9/2011 | Guglielmi et al. |
| 8,016,869 B2 | 9/2011 | Nikolchev |
| 8,021,416 B2 | 9/2011 | Abrams |
| 8,043,326 B2 | 10/2011 | Hancock et al. |
| 8,048,104 B2 | 11/2011 | Monstadt et al. |
| RE43,311 E | 4/2012 | Wallace et al. |
| 8,157,855 B2 | 4/2012 | Eidenschink et al. |
| 8,202,292 B2 | 6/2012 | Kellett |
| 8,221,396 B2 | 7/2012 | Dehnad et al. |
| 8,221,483 B2 | 7/2012 | Ford et al. |
| 8,273,116 B2 | 9/2012 | Licata et al. |
| 8,298,256 B2 | 10/2012 | Gandhi et al. |
| 8,328,860 B2 | 12/2012 | Strauss et al. |
| 8,372,110 B2 | 2/2013 | Monstadt et al. |
| 8,398,671 B2 | 3/2013 | Chen et al. |
| 8,425,541 B2 | 4/2013 | Masters et al. |
| 8,470,013 B2 | 6/2013 | Duggal et al. |
| 8,480,701 B2 | 7/2013 | Monstadt |
| 8,562,667 B2 | 10/2013 | Cox |
| 8,597,321 B2 | 12/2013 | Monstadt et al. |
| 8,632,584 B2 | 1/2014 | Henkes et al. |
| 8,641,746 B2 | 2/2014 | Andreas et al. |
| 8,641,777 B2 | 2/2014 | Strauss et al. |
| 8,652,163 B2 | 2/2014 | Padilla et al. |
| 8,657,870 B2 | 2/2014 | Turovskiy et al. |
| 8,715,312 B2 | 5/2014 | Burke et al. |
| 8,715,317 B1 | 5/2014 | Janardhan et al. |
| 8,721,625 B2 | 5/2014 | Klint |
| 8,728,142 B2 | 5/2014 | Gandhi et al. |
| 8,777,978 B2 | 7/2014 | Strauss et al. |
| 8,777,979 B2 | 7/2014 | Shrivastava et al. |
| 8,795,320 B2 | 8/2014 | Strauss et al. |
| 8,795,321 B2 | 8/2014 | Strauss et al. |
| 8,801,747 B2 | 8/2014 | Strauss et al. |
| 8,845,676 B2 | 9/2014 | Monstadt et al. |
| 8,864,790 B2 | 10/2014 | Strauss et al. |
| 8,870,909 B2 | 10/2014 | Cox |
| 8,876,863 B2 | 11/2014 | Eskridge |
| 8,900,285 B2 | 12/2014 | Licata |
| 8,906,057 B2 | 12/2014 | Connor et al. |
| 8,915,950 B2 | 12/2014 | Cam et al. |
| 8,926,681 B2 | 1/2015 | Levy et al. |
| 8,932,317 B2 | 1/2015 | Marks et al. |
| 8,940,011 B2 | 1/2015 | Teoh et al. |

(56) References Cited

U.S. PATENT DOCUMENTS

| | | |
|---|---|---|
| 8,974,509 B2 | 3/2015 | Licata |
| 8,974,513 B2 | 3/2015 | Ford et al. |
| 8,992,563 B2 | 3/2015 | Chen |
| 8,998,926 B2 | 4/2015 | Pomeranz |
| 9,039,749 B2 | 5/2015 | Shrivastava et al. |
| 9,050,095 B2 | 6/2015 | Monstadt et al. |
| 9,055,948 B2 | 6/2015 | Jaeger et al. |
| 9,211,202 B2 | 12/2015 | Strother et al. |
| 9,486,224 B2 | 11/2016 | Riina et al. |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 10,828,039 B2 | 11/2020 | Rhee et al. |
| 2001/0000797 A1 | 5/2001 | Mazzocchi |
| 2001/0001835 A1 | 5/2001 | Greene et al. |
| 2002/0151883 A1 | 10/2002 | Guglielmi |
| 2003/0014073 A1 | 1/2003 | Bashiri et al. |
| 2003/0018294 A1 | 1/2003 | Cox |
| 2003/0028209 A1 | 2/2003 | Teoh et al. |
| 2003/0040733 A1 | 2/2003 | Cragg et al. |
| 2003/0040772 A1 | 2/2003 | Hyodoh et al. |
| 2003/0060833 A1 | 3/2003 | Carrison et al. |
| 2003/0176857 A1 | 9/2003 | Lee |
| 2003/0212426 A1 | 11/2003 | Olson et al. |
| 2003/0225365 A1 | 12/2003 | Greff et al. |
| 2004/0002731 A1 | 1/2004 | Aganon et al. |
| 2004/0002733 A1 | 1/2004 | Teoh |
| 2004/0225279 A1 | 11/2004 | Raymond |
| 2004/0236344 A1 | 11/2004 | Monstadt et al. |
| 2005/0079196 A1 | 4/2005 | Henkes et al. |
| 2005/0267511 A1 | 12/2005 | Marks et al. |
| 2006/0036281 A1 | 2/2006 | Patterson et al. |
| 2006/0100602 A1 | 5/2006 | Klint |
| 2006/0135986 A1 | 6/2006 | Wallace et al. |
| 2006/0155323 A1 | 7/2006 | Porter et al. |
| 2006/0200234 A1 | 9/2006 | Hines |
| 2006/0206199 A1 | 9/2006 | Churchwell et al. |
| 2006/0271097 A1 | 11/2006 | Ramzipoor et al. |
| 2006/0276834 A1* | 12/2006 | Balgobin ......... A61B 17/12022 606/200 |
| 2007/0073334 A1 | 3/2007 | Ramzipoor |
| 2007/0100426 A1 | 5/2007 | Rudakov et al. |
| 2007/0175536 A1 | 8/2007 | Monetti et al. |
| 2007/0191924 A1 | 8/2007 | Rudakov |
| 2008/0045922 A1 | 2/2008 | Cragg et al. |
| 2008/0051803 A1 | 2/2008 | Monjtadt et al. |
| 2008/0103585 A1 | 5/2008 | Monstadt et al. |
| 2008/0125855 A1 | 5/2008 | Henkes et al. |
| 2008/0221654 A1* | 9/2008 | Buiser ............. A61B 17/12145 606/191 |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0143786 A1 | 6/2009 | Bashiri et al. |
| 2009/0227976 A1 | 9/2009 | Calabria et al. |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0144895 A1 | 6/2010 | Porter |
| 2010/0256666 A1 | 10/2010 | Chen et al. |
| 2010/0268204 A1 | 10/2010 | Tieu et al. |
| 2010/0331948 A1 | 12/2010 | Turovskiy et al. |
| 2011/0098814 A1 | 4/2011 | Monstadt et al. |
| 2011/0106128 A1 | 5/2011 | Chen |
| 2011/0118768 A1 | 5/2011 | Tran et al. |
| 2011/0118777 A1 | 5/2011 | Patterson et al. |
| 2011/0137405 A1 | 6/2011 | Wilson et al. |
| 2011/0184453 A1 | 7/2011 | Levy et al. |
| 2012/0010648 A1 | 1/2012 | Monstadt et al. |
| 2012/0209310 A1 | 8/2012 | Chen et al. |
| 2012/0271344 A1 | 10/2012 | Ford et al. |
| 2012/0316632 A1 | 12/2012 | Gao |
| 2013/0138198 A1 | 5/2013 | Aporta et al. |
| 2013/0184743 A1 | 7/2013 | Chen et al. |
| 2013/0211492 A1 | 8/2013 | Schneider et al. |
| 2013/0274866 A1 | 10/2013 | Cox et al. |
| 2014/0005651 A1 | 1/2014 | Eskridge |
| 2014/0012307 A1 | 1/2014 | Franano et al. |
| 2014/0039535 A1 | 2/2014 | Eskuri |
| 2014/0058420 A1 | 2/2014 | Hannes et al. |
| 2014/0135818 A1 | 5/2014 | Gandhi et al. |
| 2014/0142608 A1 | 5/2014 | Eskridge et al. |
| 2014/0148843 A1 | 5/2014 | Strauss et al. |
| 2014/0163604 A1 | 6/2014 | Monstadt |
| 2014/0236217 A1 | 8/2014 | Gandhi et al. |
| 2014/0277092 A1 | 9/2014 | Teoh et al. |
| 2014/0277094 A1 | 9/2014 | Chen et al. |
| 2014/0288633 A1 | 9/2014 | Burke et al. |
| 2014/0316012 A1 | 10/2014 | Freyman et al. |
| 2014/0371734 A1 | 12/2014 | Truckai |
| 2014/0371839 A1 | 12/2014 | Henkes et al. |
| 2015/0005804 A1 | 1/2015 | Franano et al. |
| 2015/0057700 A1 | 2/2015 | Chen et al. |
| 2015/0066073 A1 | 3/2015 | Ma |
| 2015/0105817 A1 | 4/2015 | Marchand et al. |
| 2015/0133990 A1 | 5/2015 | Davidson |
| 2015/0142042 A1 | 5/2015 | Cox |
| 2015/0150563 A1 | 6/2015 | Marchand et al. |
| 2015/0157331 A1 | 6/2015 | Levy et al. |
| 2015/0164665 A1 | 6/2015 | Cam et al. |
| 2015/0173771 A1 | 6/2015 | Marks et al. |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0028109 A1 | 2/2018 | Tesnow |
| 2018/0028190 A1* | 2/2018 | Ozasa ................. A61M 37/00 |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |

FOREIGN PATENT DOCUMENTS

| | | |
|---|---|---|
| EP | 1884208 A1 | 2/2008 |
| EP | 2668914 A1 | 12/2013 |
| WO | 2011066962 A1 | 6/2011 |
| WO | 2014078286 A1 | 5/2014 |
| WO | 2017074411 A1 | 5/2017 |
| WO | 2018051187 A1 | 3/2018 |

* cited by examiner

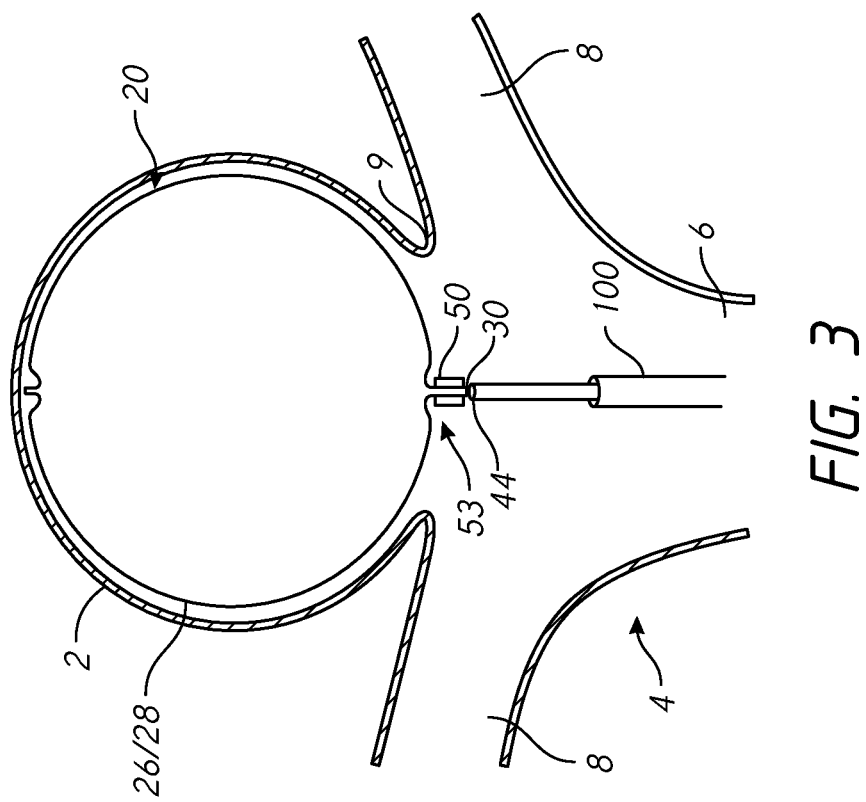
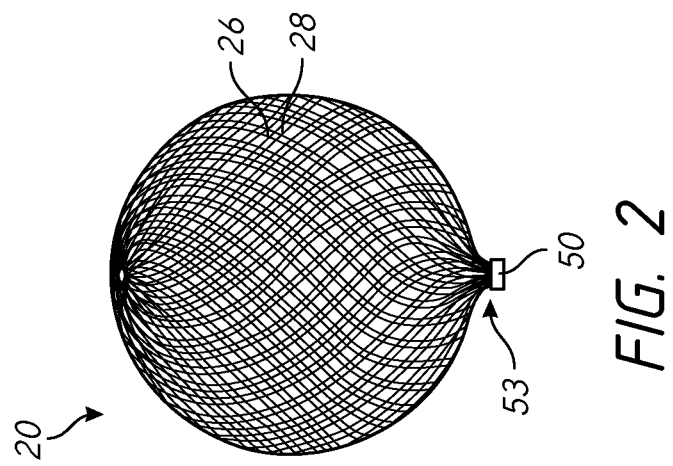

ELECTROLYTIC DETACHMENT FOR IMPLANTABLE DEVICES

CROSS-REFERENCE TO RELATED APPLICATIONS

This application is a continuation of U.S. patent application Ser. No. 15/616,981, filed Jun. 8, 2017, which claims the benefit of priority of U.S. Provisional Patent Application No. 62/354,968 filed Jun. 27, 2016, both of which are hereby incorporated by reference in their entirety.

FIELD

The subject technology relates to the delivery of implantable medical devices and systems for delivering implantable medical devices.

BACKGROUND

The use of endovascular techniques for the implantation of medical devices for treatment, e.g., by occlusion, of body cavities such as arteries, veins, fallopian tubes or vascular deformities is known in the art. For example, vascular aneurysms can be occluded with an implant that is introduced with a delivery wire through a catheter. Once advanced to the treatment site, the implant is inserted into the aneurysm cavity to occlude the aneurysm and then detached from the delivery wire.

SUMMARY

Electrolytic detachment of an implant from a delivery system can leave a portion of a delivery wire protruding from the implant after detachment, presenting a risk of harm to the surrounding anatomy. An implant can be attached to a delivery wire in a manner that minimizes an extent to which a distal region of the delivery wire protrudes from the implant after the implant is detached from a proximal region of the delivery wire. For example, an implant can be connected to a distal end of a delivery wire such that a severed distal portion of the delivery wire is retracted into an interior space of the implant upon severance of the implant from the proximal region of the delivery wire. Such an arrangement advantageously can reduce the extent of protrusion compared to an attachment that does not provide retraction capability.

The subject technology is illustrated, for example, according to various aspects described below. Various examples of aspects of the subject technology are described as numbered clauses (1, 2, 3, etc.) for convenience. These are provided as examples and do not limit the subject technology.

Clause 1. An implant comprising:
a proximal end portion defining a lumen; and
an expansion member located distal to the proximal end portion and proximal to a distal region of a delivery wire, the distal region being distal to the proximal end portion, the expansion member being biased to move the distal region of the delivery wire distally away from the proximal end portion;
wherein at least a portion of the delivery wire extends entirely through the lumen.

Clause 2. The implant of clause 1, wherein the expansion member comprises a spring.

Clause 3. The implant of any of the previous clauses, wherein a distal cross-sectional dimension of the distal region is greater than a lumen cross-sectional dimension of the lumen.

Clause 4. The implant of any of the previous clauses, wherein the distal region of the delivery wire comprises an electrolytically corrodible section.

Clause 5. The implant of any of the previous clauses, wherein the delivery wire comprises a detachment zone proximal to the proximal end portion.

Clause 6. The implant of clause 5, wherein a distal cross-sectional dimension of the distal region is greater than a proximal cross-sectional dimension of the detachment zone.

Clause 7. The implant of clause 5, further comprising a coating layer that electrically insulates the detachment zone of the delivery wire from the proximal end portion.

Clause 8. A delivery system comprising:
an implant having a proximal end portion;
a delivery wire having (i) a detachment zone proximal to the proximal end portion, and (ii) a distal region distal to the proximal end portion;
an expansion member located between the proximal end portion and the distal region of the delivery wire, the expansion member being biased to move the distal region of the delivery wire distally away from the proximal end portion; and
a catheter, wherein at least a portion of the delivery wire is within the catheter.

Clause 9. The implant of clause 8, wherein the expansion member comprises a spring.

Clause 10. The implant of any of clauses 8-9, wherein the proximal end portion defines a lumen, and at least a portion of the delivery wire extends entirely through the lumen.

Clause 11. The implant of any of clauses 8-10, wherein a distal cross-sectional dimension of the distal region is greater than a lumen cross-sectional dimension of the lumen.

Clause 12. The implant of any of clauses 8-11, wherein the distal region of the delivery wire comprises an electrolytically corrodible section.

Clause 13. The implant of an of clauses 8-12, wherein a distal cross-sectional dimension of the distal region is greater than a proximal cross-sectional dimension of the detachment zone.

Clause 14. The implant of any of clauses 8-13, further comprising a coating layer that electrically insulates the detachment zone of the delivery wire from the proximal end portion.

Clause 15. A method of delivering an implant, the method comprising:
positioning the implant at a target location within a patient, the implant being attached to a delivery wire having (i) a proximal region, (ii) a detachment zone proximal to a proximal end portion of the implant, and (iii) a distal region distal to the proximal end portion, the implant having an expansion member located between the proximal end portion and a distal region of the delivery wire, the expansion member being biased to move the distal region of the delivery wire distally away from the proximal end portion;
separating the distal region from the proximal region at the detachment zone; and
advancing the distal region distally away from the proximal end portion.

Clause 16. The method of clause 15, wherein separating the implant comprises electrolytically corroding a portion of the delivery wire.

Clause 17. The method of an of clauses 15-16, wherein positioning the implant comprises applying a distally directed force to the proximal end portion and a proximally directed force to the delivery wire.

Clause 18. The method of any of clauses 15-17, wherein applying a distally directed force to the proximal end portion comprises pushing the proximal end portion with a catheter.

Clause 19. The method of any of clauses 15-18, wherein at least a portion of the delivery wire is within the catheter during the separating.

Clause 20. The method of any of clauses 15-19, wherein the advancing the distal region comprises advancing the detachment zone and the distal region of the delivery wire to be entirely distal to a proximal end of the proximal end portion.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplifying and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 2 shows a side view of a braid ball implant, in accordance with one or more embodiments of the present disclosure.

FIG. 3 shows a sectional view of the braid ball implant of FIG. 2 deployed within a bifurcation aneurysm, in accordance with one or more embodiments of the present disclosure.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

In accordance with some embodiments of the subject technology an implant can be attached to a delivery wire in a manner that minimizes an extent to which a distal region of the delivery wire protrudes from the implant after the implant is detached from a proximal region of the delivery wire. For example, an implant can be connected to a distal end of a delivery wire such that a severed distal region of the delivery wire is retracted into an interior space of the implant upon severance of the implant from the proximal region of the delivery wire. Such an arrangement advantageously can reduce the extent of protrusion compared to an attachment that does not provide retraction capability.

Figure 1A:
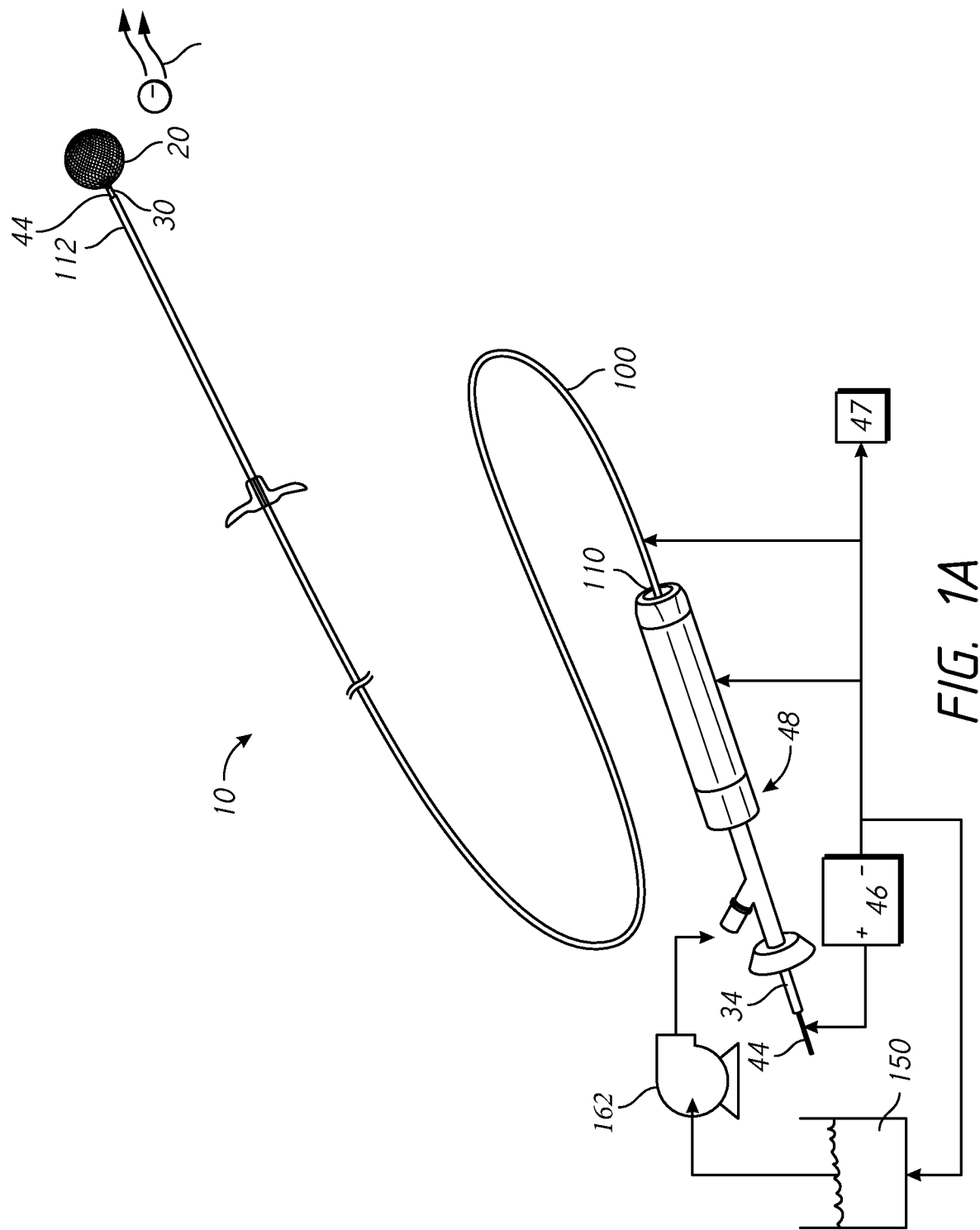
FIG. 1A shows a perspective view of a delivery system, in accordance with one or more embodiments of the present disclosure.
Figure 1B:
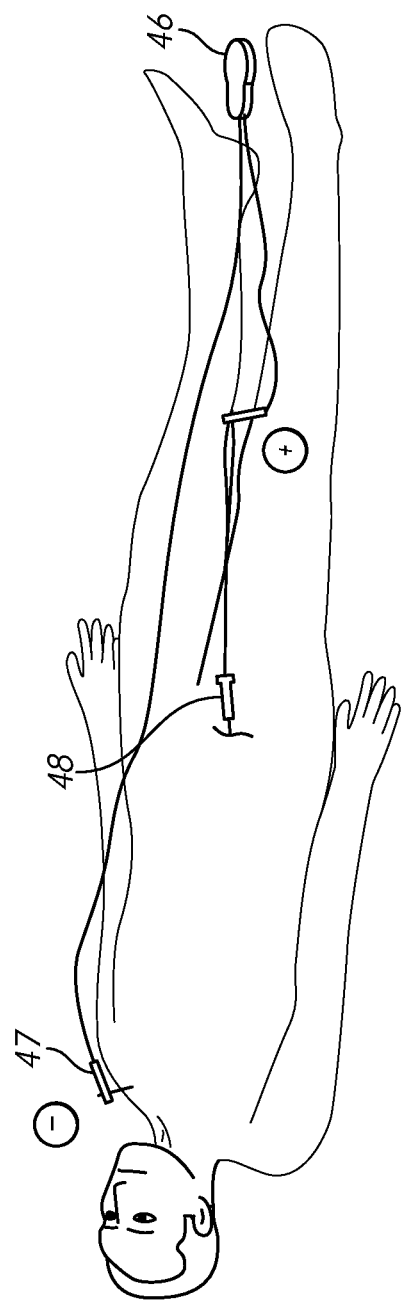
FIG. 1B shows a perspective view of the delivery system of FIG. 1A with respect to a patient, in accordance with one or more embodiments of the present disclosure.

Referring to FIGS. 1A-B, illustrated are various views of a delivery system 10, according to one or more embodiments of the subject technology. More particularly, FIG. 1A depicts a view of a delivery system 10, and FIG. 1B depicts a view of the same delivery system in connection with a patient. According to some embodiments, a delivery system 10 can include an implant 20, and a delivery catheter 100 connected to a handle 48. The handle 48 shown provides proximal access to a delivery wire 44 that is connected to the implant 20 at a distal end thereof. The implant 20, attached to the distal end of the delivery wire 44, is advanced in the longitudinal direction in the delivery catheter 100 to the treatment site. Common treatment sites include blood vessels, particularly those in the neurovasculature such as aneurysms.

According to some embodiments, for example as shown in FIGS. 1A-B, the delivery catheter 100 can be formed as a generally tubular member with a body extending from a proximal end 110 and terminating in a distal end 112. Several commercially available microcatheter designs are suitable for the use in the disclosed embodiments. A microcatheter suitable for neurovascular use has a length that is at least 125 cm long, and more particularly may be between about 125 cm and about 175 cm long. Typically the delivery catheter 100 is about 155 cm long. An inner lumen of the delivery catheter 100 generally has an inner diameter between about 0.01 inch and about 0.098 inch (0.25-2.49 mm). Other designs and dimensions are contemplated. Commercially available microcatheters which may be suitable for use as delivery catheters include the REBAR™ Reinforced Micro Catheter and the MARKSMAN™ Catheter, both of which are available from Medtronic Inc. (Irvine, CA).

A power supply 46 can be coupled to the delivery system 10. A current can flow from the power supply 46 along a delivery wire 44 to a detachment zone 30. The detachment zone 30 can comprise a longitudinally extending zone within which some or all of an electrolytically corrodible portion of the delivery wire 44 can be positioned, as discussed further herein. The detachment zone 30 can be between a portion of the delivery wire 44 and the implant 20. The current can flow from the detachment zone 30 to a return path, optionally via a structure extending near the detachment zone 30. For example, the power supply 46 can be coupled to a portion of the delivery wire 44 extending proximally of the handle 48, and the delivery wire 44 can conduct the electrically current to or from the detachment zone 30. Alternatively or in combination, the power supply 46 also can be coupled to, and electrical current can be conducted by, the delivery wire 44, the handle 48, the delivery catheter 100, the fluid source 150, and/or the patient via a region 47 on the surface of the patient's skin to provide a conductive pathway between the detachment zone 30 and the power supply 46 or ground. For example, a positive terminal of a direct current power supply 46, for example as shown in FIG. 1A, may be coupled to the portion of the delivery wire 44 extending proximally of the handle 48, and a negative terminal of a direct current power supply 46 or ground may be coupled to the handle 48, the delivery catheter 100, the fluid source 150, and/or the patient via the region 47. In embodiments wherein the delivery wire 44, the handle 48, and/or the delivery catheter 100 are attached, directly or indirectly, to the power supply 46 or ground to conduct electrical current, they can comprise electrically conductive materials and/or components for conduction of electrical current between the detachment zone and the power supply or ground. Similarly, in embodiments wherein fluid conducts electrical current between the detachment zone and the power supply or ground, the fluid source 150 can comprise an electrically conductive fluid.

According to some embodiments, the power supply 46 can include an electrical generator configured to output an electrical current that is sufficient to detach the implant 20 by electrolytic corrosion. The power supply 46 may be a direct current power supply, an alternating current power supply, or a power supply switchable between a direct current and an alternating current. The power supply 46 can include a suitable controller that can be used to control various parameters of the energy output by the generator, such as intensity, amplitude, duration, frequency, duty cycle, and polarity. For example, the power supply 46 can provide a voltage of about 12 volts to about 28 volts and a current of about 1 mA to about 2 mA.

According to some embodiments, for example as shown in FIG. 1A, a fluid source 150 may be provided in connection with a pump 162 for infusion of the fluid 170 via the delivery catheter 100. The fluid source 150 can be saline or another sterile, electrolytic, biocompatible solution. The fluid can be infused together with a drug such as heparin. The fluid may be drawn from the fluid source 150 into the pump 162 and provided to a lumen of the delivery catheter 100. The pump 162 can be an infusion pump, a pressurized container, and/or a gravity-based infusion mechanism. According to some embodiments, for example as shown in FIGS. 1A and 1B, current can be provided from the power supply 46 via the delivery wire 44 to the detachment zone 30, as discussed in more detail below. While the implant 20 and the detachment zone 30 are within the patient, the current from the detachment zone 30 may flow through tissue of the patient until the current reaches a terminal of the power supply 46 that is connected to the patient at a region 47. For example, the terminal (e.g, a needle) at the region 47 can be placed on or through the surface of the patient's skin to provide a conductive pathway from the detachment zone 30 at or near the implant 20 to ground or to the power supply 46.

According to some embodiments, for example as shown in FIGS. 2 and 3, an implant 20 delivered by the delivery system 10 can be a braid ball implant. The implant 20 can be formed from tubular braid stock including a resilient material, such as nitinol, that defines an open volume in an uncompressed/unconstrained state. The size of the implant can be selected to fill an aneurysm 2. The implant 20 can include a hub 50 at a proximal end 53 thereof. The hub 50 can be fixedly attached to the remainder of the implant 20. The implant 20 can include layers 26, 28 at least where impacted by flow at the neck 9 of the aneurysm 2.

According to some embodiments, the implant 20 can be placed within an aneurysm 2 at a vascular bifurcation 4, formed by trunk vessel 6 and branch vessels 8, for example as illustrated in FIG. 3. The implant 20 can be delivered by access through the trunk vessel 6 (e.g., the basilar artery), preferably through a commercially available microcatheter with a delivery system as detailed below. To deliver the implant 20, the delivery wire 44 is positioned such that the implant 20 can be delivered at least partially into the aneurysm 2. When the implant is positioned in the aneurysm, the implant 20 is separated from a proximal portion of the delivery wire 44 by electrolytic corrosion, and a distal portion of the delivery wire 44 is withdrawn into the delivery catheter 100.

While the implant 20 illustrated herein is a braided ball, the implant 20 can be any well-known treatment device including, but not limited to, a vasoocclusive coil, a stents, filters, or flow diverters.

Figure 4A:
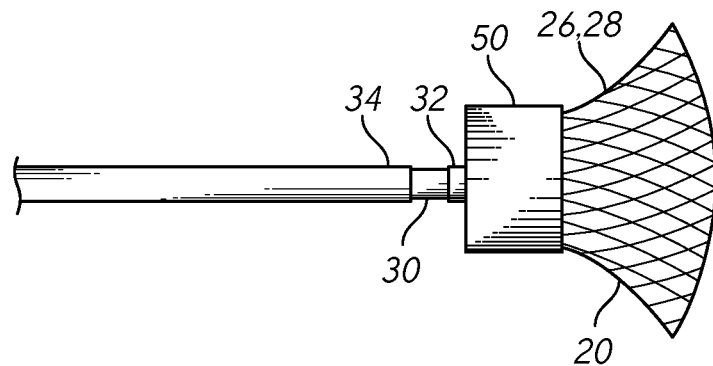
FIG. 4A shows a side view of a distal end of the delivery system of FIG. 1, in accordance with one or more embodiments of the present disclosure.
Figure 4B:
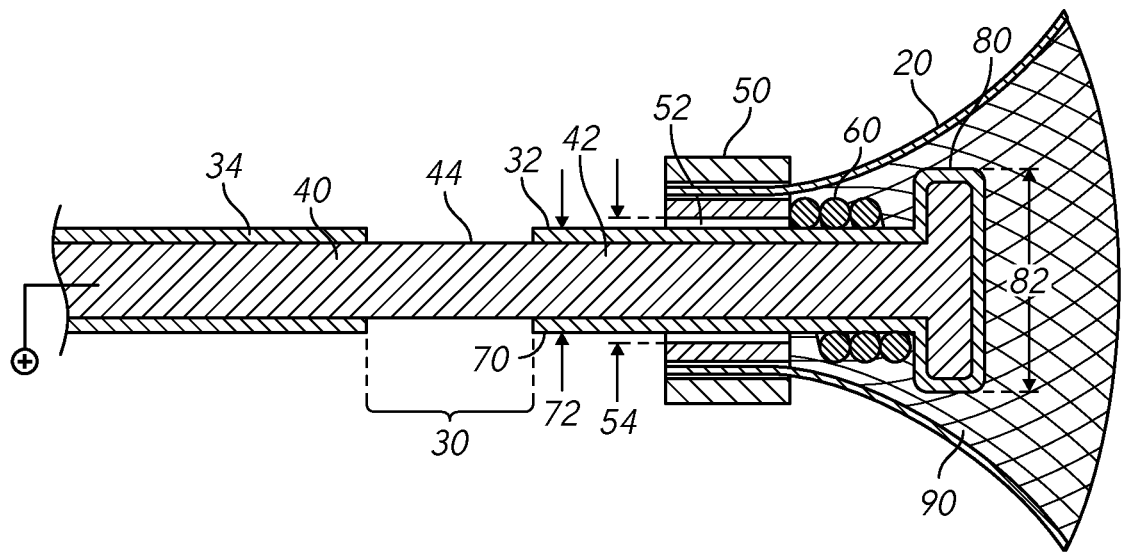
FIG. 4B shows a sectional view of the distal end of the delivery system shown in FIG. 4A in an attached state, in accordance with one or more embodiments of the present disclosure.
Figure 5:
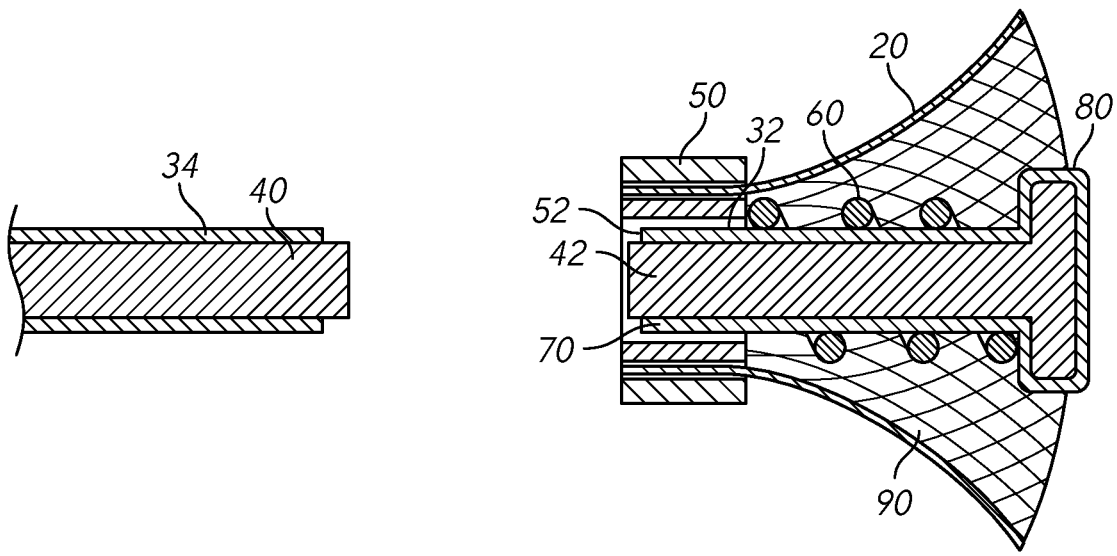
FIG. 5 shows a sectional view of the distal end of the delivery system shown in FIG. 4A in a detached state, in accordance with one or more embodiments of the present disclosure.

FIGS. 4A-5 illustrate various views of a delivery wire 44 and implant 20 according to one or more embodiments of the subject technology. More particularly, FIG. 4A depicts a side view of the delivery wire 44 and implant 20, FIG. 4B depicts a sectional view of the delivery wire 44 and implant 20 in an attached state, and FIG. 5 depicts a sectional view of the delivery wire 44 and implant 20 in a detached state. Upon separation of a proximal portion of the delivery wire 44 from the implant 20, a spring force from a compression spring and applied to the distal portion of the delivery wire 44 can retract the distal portion of the delivery wire 44 into the implant 20 as described further herein. As a result, the distal portion of the delivery wire 44 is retained securely within the implant 20. The extent to which the delivery wire 44 protrudes proximally of the implant 20 is thereby reduced when compared to an arrangement that does not achieve such retraction.

According to some embodiments, for example as shown in FIGS. 4A-4B, the delivery wire 44 (e.g., core member, pusher device, etc.) has a proximal region 40, a distal region 42, and a detachment zone 30 between the proximal region 40 and the distal region 42. The delivery wire 44 can be formed of a single, monolithic component that spans across the proximal region 40, the distal region 42, and the detachment zone 30. Alternatively, the delivery wire 44 can be formed of separate segments that are joined together at any location thereon.

According to some embodiments, portions of the delivery wire 44 can be coated with a nonconductive material so that only a limited portion of surface area of the delivery wire is exposed to, and in electrical communication with, the electrolyte for corrosion when a voltage potential is applied. Limiting the size of the exposed portion of the surface area of the delivery wire can concentrate electrolytic activity to expedite corrosion through and severance of the delivery wire. A proximal insulating layer 34 can be provided over at least a portion of an outer surface of the proximal region 40. For example, the proximal insulating layer 34 can circumferentially surround an outer surface of the proximal region 40 extending proximally from a proximal end of the detachment zone 30 to a location at or near a proximal end of the delivery wire 44. Similarly, a distal insulating layer 32 can be provided over at least a portion of an outer surface of the distal region 42 extending distally from a distal end of the detachment zone 30 to a distal terminal end of the delivery wire 44. For example, the distal insulating layer 32 can circumferentially surround and cover the entire outer surface of the distal region 42.

According to some embodiments, proximal and distal insulating layers 34, 32 leave exposed the detachment zone 30 between the proximal region 40 and the distal region 42. When in contact with a body fluid, such as blood, the fluid serves as an electrolyte allowing current to be focused on the non-coated detachment zone 30. The proximal and distal insulating layers 34, 32 prevent exposure of the proximal region 40 and the distal region 42 to the fluid. Accordingly, electrical energy conducted along the delivery wire 44 is concentrated at the detachment zone 30, thereby reducing the time required to erode away the detachment zone 30. The proximal and distal insulating layers 34, 32 can be overmolded, co-extruded, sprayed on, or dip-coated with respect to the proximal region 40 and/or the distal region 42.

The distal insulating layer 32 also prevents electrical connection between the delivery wire 44 and the implant 20. As shown in FIGS. 4A-4B, the distal insulating layer 32 electrically isolates the implant 20 from an electrical current conducted along a length of the delivery wire 44, from the proximal region 40 and the distal region 42. A proximal end of the distal insulating layer 32 may be positioned at or proximal to the hub 50, and a distal end of the distal insulating layer 32 may be positioned at or distal to the hub 50. Likewise, a proximal end of the distal region 42 may be positioned proximal to the hub 50, and a distal end of the distal region 42 may be positioned within or distal to the hub 50. The distal insulating layer 32 insulates the distal region 42 from the hub 50 to prevent the electrical current from being conducted to the implant 20.

The proximal and distal insulating layers 34, 32 can be of an electrically nonconductive or insulative polymer, such as polyimide, polypropylene, polyolefins, and combinations thereof. In some embodiments, the proximal and distal insulating layers 34, 32 can be applied as a single coating with a portion thereof subsequently removed to expose the detachment zone 30. Laser ablation can be employed to selectively remove the coating to a controlled length, minimizing the time required to erode through the component. Lengths as small as 0.0005" and as large as 0.1" or longer can be removed. According to some embodiments, lengths of detachment zone 30 can be greater than 0.005" and/or less than 0.010" to provide sufficient exposure to achieve detachment times of less than 30 seconds.

The delivery wire 44 (including some or all of the proximal region 40, the distal region 42, or the detachment region 30) can comprise one or more of the following materials: ceramic materials, plastics, base metals or alloys thereof, or combinations thereof. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. In some embodiments, the electrolytically corrodible detachment zone 30 can be pre-corroded by etching or other methods.

According to some embodiments, for example as shown in FIG. 4B, the delivery wire 44 can be continuous at least through the proximal region 40. Accordingly, an electrical potential can be generated at the proximal end of the delivery wire 44 and an electrical current can be conducted through the delivery wire 44 between the proximal region 40 and the detachment zone 30. Furthermore, an axial force applied to the delivery wire 44 can result in an axial movement of the detachment zone 30 and/or the implant 20. Alternatively or in combination, axial forces can be applied to the implant 20 by other devices, such as the delivery catheter 100.

According to some embodiments, for example as shown in FIG. 4B, a proximal section 70 of the distal region 42 can extend through a lumen 52 of the hub 50. The proximal section 70 can have a proximal outer cross-sectional dimension 72 along at least the portions thereof within the hub 50 and extending proximally from the hub to the detachment zone 30. The proximal cross-sectional dimension 72 can be smaller than an inner cross-sectional dimension 54 of the lumen 52 within the hub 50. At least a portion of the proximal section 70 can freely move within the lumen 52 to provide axial (i.e., proximal and/or distal) mobility within the lumen 52.

According to some embodiments, a distal section 80 of the distal region 42 can be located distal to the hub 50 the distal section 80 can have a distal outer cross-sectional dimension 82 that is greater than the proximal outer cross-sectional dimension 72 and/or the inner cross-sectional dimension 54 of the lumen 52. The dimensions of the distal section 80 can prevent the distal section 80 and other sections attached thereto from moving entirely through the lumen 52 of the hub 50. Furthermore, the distal outer cross-sectional dimension 82 can be greater than any opening, aperture, interstice, port, or window separating the inner cavity 90 of the implant 20 from an external environment. Accordingly, once the implant 20 is fully formed, the distal section 80 and any components attached thereto can be prevented from moving entirely out of the inner cavity 90 of the implant 20.

According to some embodiments, an expansion member 60, or a portion thereof, can be located between at least a portion of the distal section 80 and at least a portion of the hub 50. The expansion member 60 can be or include a spring or other mechanism for providing elastic forces. For example, the spring can be a compression spring that responds to a compression load by shortening or reducing its length. The expansion member 60 can include a helical coil that has a spring constant. Alternatively or in combination, the expansion member 60 can be an axially and/or circumferentially continuous material (e.g., tube, strut, braid, etc.) with elastic properties. The expansion member 60 can store potential energy when placed in certain configurations to provide a bias toward a relaxed state. The bias may include a tendency to axially elongate after the expansion member 60 is axially compressed. Accordingly, the extension member 60 can be biased to move axially adjacent structures axially away from each other. For example, the expansion member 60 can be seated against and/or placed between the hub 50 and the distal section 80. The expansion member 60 can be axially compressed by moving the distal section 80 and the hub 50 toward each other. For example, the distal section 80 can be moved proximally relative to the hub 50 and/or the hub 50 can be move distally relative to the distal section 80. Axial forces can be applied to the distal section 80 by, for example, other portions of the delivery wire 44, such as the proximal region 40 of the delivery wire 44. Axial forces can be applied to the hub 50 by, for example, other devices, such as the delivery catheter 100, as discussed further herein.

According to some embodiments, for example as shown in FIG. 5, the proximal region 40 of the delivery wire 44 can be separated from the distal region 42 of the delivery wire 44 at the detachment zone 30. Separation at the detachment zone 30 can be achieved by electrolytic corrosion, mechanical release, chemical reactions, thermal activity, or combinations thereof. The result of the separation can include the complete separation of (a) the implant 20, including the hub 50, and the distal region 42 of the delivery wire 44, including the distal insulating layer 32, the proximal section 70, and the distal section 80, from (b) the proximal region 40 of the delivery wire 44, including the proximal insulating layer 34 and/or other components along the delivery wire 44. Portions of the detachment zone 30 that are not completely removed can remain attached to portions of the proximal region 40 and/or the distal region 42. For purposes of discussion herein, such remaining portions of the detachment zone 30 can be considered, after separation, components of the proximal region 40 and/or the distal region 42.

According to some embodiments, after separation at the detachment zone 30, the expansion member 60 can act on the hub 50 and the distal section 80 to achieve distally directed movement of the distal section 80 and/or the proximal section 70. After separation, the expansion member 60 can be permitted to freely expand to achieve a relaxed state. The distally directed movement of the distal section 80 and/or the proximal section 70 can continue until a proximalmost terminal end of the proximal section 70 is distal to a proximal most terminal end of the hub 50 and/or the lumen 52. The distally directed movement of the distal section 80 and/or the proximal section 70 can continue until a proximalmost terminal end of the proximal section 70 is entirely distal to the hub 50 and/or within the interior cavity 90 of the implant 20. According to some embodiments, the proximal section 70 and the distal section 80 can freely move within the cavity 90 of the implant 20 after separation. The dimensions of the distal section 80 and/or the proximal section 70 can exceed the dimensions of the lumen 52 and/or other openings between the cavity 90 in an external environment of the implant 20, such that the distal section 80 and the proximal section 70 are retained within the interior cavity 90 of the implant 20.

Figure 6:
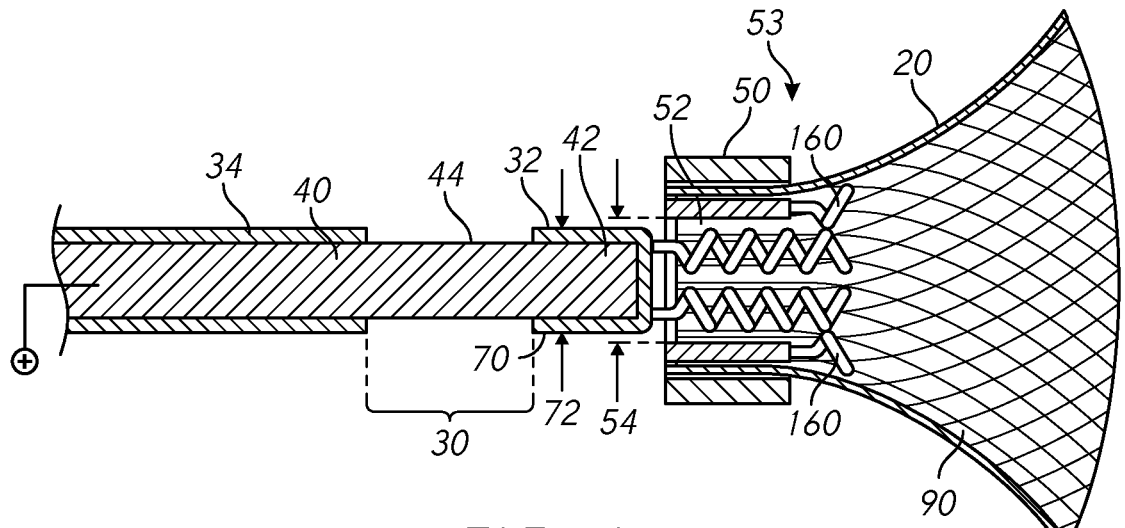
FIG. 6 shows a sectional view of a distal end of a delivery system, similar in some respects to the delivery system of FIGS. 4A and 4B, in an attached state, in accordance with one or more embodiments of the present disclosure.
Figure 7:
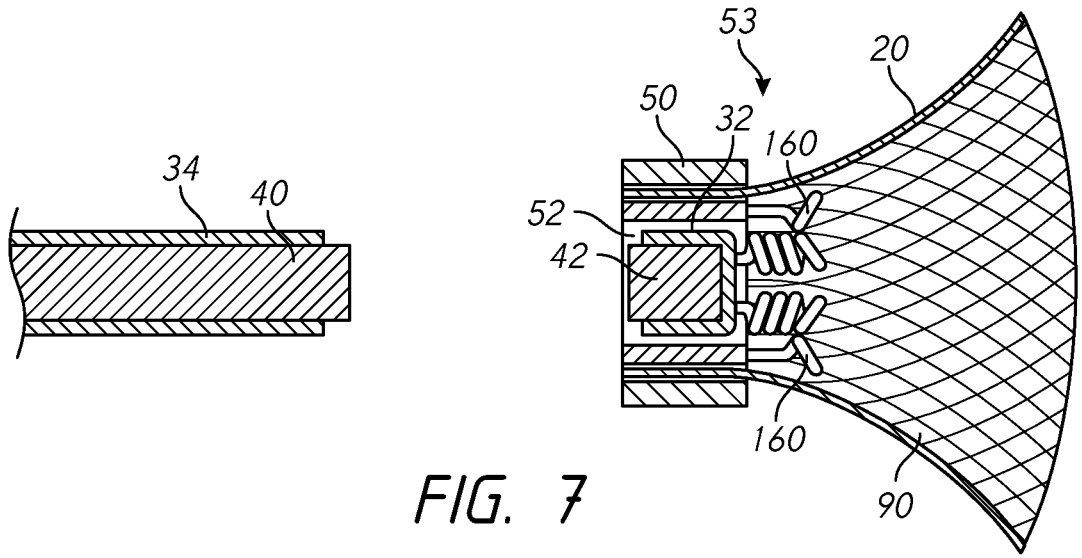
FIG. 7 shows a sectional view of the distal end of the delivery system shown in FIG. 6 in a detached state, in accordance with one or more embodiments of the present disclosure.

FIGS. 6 and 7 illustrate various views of an exemplifying delivery wire 44 and implant 20 according to one or more embodiments of the subject technology. More particularly, FIG. 6 depicts a sectional view of the delivery wire 44 and implant 20 in an attached configuration, and FIG. 7 depicts a sectional view of the delivery wire 44 and implant 20 in a detached configuration. Upon separation of a proximal portion of the delivery wire 44 from the implant 20, a spring force from a tension spring and applied to the distal portion of the delivery wire 44 can retract the distal portion of the delivery wire 44 into the implant 20 as described further herein. While FIGS. 4A-5 illustrate a delivery wire 44 and implant 20 with a compression spring, the delivery wire 44 and implant 20 can be used with a tension spring, for example as illustrated in part in FIGS. 6 and 7, according to one or more embodiments of the subject technology. Therefore, the delivery wire 44, the implant 20, and other elements and components are not described again in detail with reference to FIGS. 6-7, as these components can be readily understood from the other disclosure of them herein.

According to some embodiments, for example as shown in FIG. 6, the delivery wire 44 can provide a detachment zone 30 between the proximal insulating layer 34 and the distal insulating layer 32. According to some embodiments, for example as shown in FIG. 6, the proximal section 70 of the distal region 42 can extend through or near a lumen 52 of the hub 50. At least a portion of the proximal section 70 can freely move within the lumen 52 to provide axial (i.e., proximal and/or distal) mobility within the lumen 52.

According to some embodiments, the proximal section 70 can connect to one or more expansion members 160, or a portion thereof, can be located between at least a portion of the distal section 80 and at least a portion of the hub 50. The expansion member 160 can be or include a spring or other mechanism for providing elastic forces. For example, the spring can be a tension or extension spring that responds to a tension load by elongating or increasing its length. The expansion members 160 can include a helical coil that has a spring constant. Alternatively or in combination, the expansion member 160 can be an axially and/or circumferentially continuous material (e.g., tube, strut, braid, etc.) with elastic properties. A plurality of expansion members 160 can attach to various regions or the same region of the proximal section 70 and to various regions or the same region of the hub 50. For example, the expansion members 160 can attach to a distalmost terminal end region of the proximal section 70. The expansion members 160 can attach, for example, to the distal insulating layer 32, such that the distal region 42 is not in electrical connection with the expansion members 160. The expansion members 160 can further attached to a distalmost end region of the hub 50. The expansion members 160 can attach to the hub 50 at a variety of distributed locations along the circumference of the hub 50. According to some embodiments, for example as shown in FIG. 6, the expansion members 160 can extend within the lumen 52 of the hub 50 at least to a location distal to the hub 50 and/or within the cavity of the implant 20. The expansion members 160 can, from this location, extend proximally to the distalmost terminal end of the hub 50 attached thereto. The attachment of the expansion members 160 to the hub 50 can occur generally at the proximal end 53 of the implant 20, such that the expansion members 160 need not extend across an entire or substantial length of the implant 20. For example, the expansion members 160 can attach to the implant 20 at a proximal half of the implant 20.

The expansion member 160 can store potential energy when placed in certain configurations to provide a bias toward a relaxed state. The bias may include a tendency to axially shorten after the expansion members 160 are axially elongated. Accordingly, the expansion members 160 can be biased to move axially adjacent structures toward each other. For example, the expansion member 160 can be attached to the hub 50 and the proximal section 70. The expansion member 160 can be axially elongated by moving the proximal section 70 and the hub 50 away from each other. For example, the proximal section 70 can be moved proximally relative to the hub 50 and/or the hub 50 can be move distally relative to the proximal section 70. Axial forces can be applied to the proximal section 70 by, for example, other portions of the delivery wire 44, such as the proximal region 40 of the delivery wire 44. Axial forces can be applied to the hub 50 by, for example, other devices, such as the delivery catheter 100, as discussed further herein.

According to some embodiments, for example as shown in FIG. 7, the proximal region 40 of the delivery wire 44 can be separated from the distal region 42 of the delivery wire 44 along the detachment zone 30. According to some embodiments, after separation along the detachment zone 30, the expansion members 160 can act on the hub 50 and the proximal section 70 to achieve distally directed movement of the proximal section 70. After separation, the expansion members 160 can be permitted to freely shorten to achieve a relaxed state. The distally directed movement of the proximal section 70 can continue until a proximalmost terminal and of the proximal section 70 is distal to a proximal most terminal end of the hub 50 and/or the lumen 52. The distally directed movement of the proximal section 70 can continue until a proximalmost terminal end of the proximal section 70 is entirely distal to the hub 50 and/or within the interior cavity 90 of the implant 20. According to some embodiments, the proximal section 70 can remain attached to the hub 50 via the expansion members 160 after separation from the proximal region 40.

Figure 8:
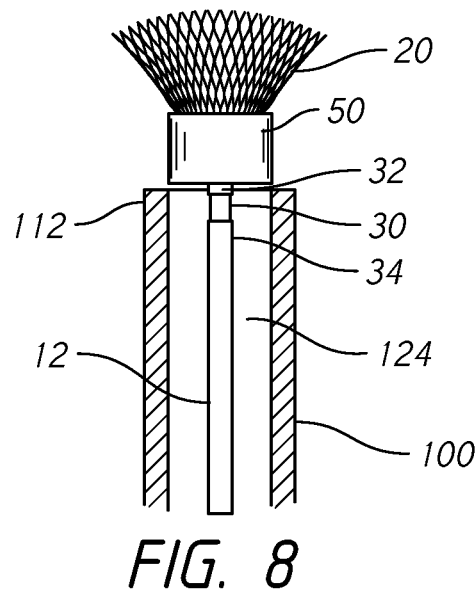
FIG. 8 shows a partial sectional view of an implant in a stage of deployment, in accordance with one or more embodiments of the present disclosure.
Figure 9:
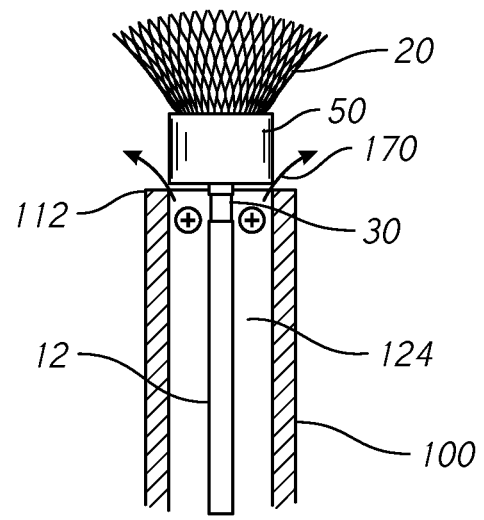
FIG. 9 shows a partial sectional view of an implant in a stage of deployment, in accordance with one or more embodiments of the present disclosure.
Figure 10:
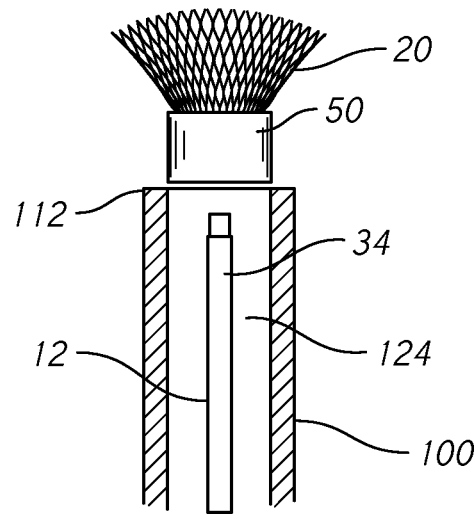
FIG. 10 shows a partial sectional view of an implant in a stage of deployment, in accordance with one or more embodiments of the present disclosure.

FIGS. 7-10 illustrate various stages of an exemplifying method according to one or more embodiments of the subject technology. More particularly, FIG. 8 illustrates an implant 20 connected to a delivery wire 44, FIG. 9 illustrates detachment in progress, and FIG. 10 illustrates a state following detachment of the implant 20 from the delivery wire 44.

According to some embodiments, the implant 20 can be advanced to the target site. As shown in FIG. 8, the delivery catheter 100 can be brought to the implant 20, such that the distal end 112 of the delivery catheter 100 can contact or otherwise act on the implant 20. For example, the distal end 112 can be used to apply a distally directed force to the hub 50 while a proximally directed force is applied to the delivery wire 44. Alternatively or in combination, one of the delivery wire 44 and the implant 20 can be stabilized while the other is subjected to a force. The relative forces applied to the delivery wire 44 and the implant 20 can cause the delivery wire 44 to be moved proximally relative to the implant 20. For example, the detachment zone 30 can be located outside and proximal to the hub 50 and/or other portions of the implant 20. The detachment zone 30 may be positioned to be entirely exposed, partially exposed, or not exposed with respect to the implant 20 and/or the hub 50. Alignment of the delivery catheter detachment zone 30 may be facilitated by components providing visualization. For example, a radiopaque marker of the implant 20 can be aligned with a radiopaque marker of the delivery wire 44 while in a configuration that corresponds to proper alignment (e.g., axial alignment).

According to some embodiments, for example as shown in FIG. 9, detachment of the implant 20 from the delivery wire 44 can be achieved through electrolytic corrosion of the detachment zone 30. An electrical potential can be provided by the power supply 46 to cause electrical current to pass between the detachment zone 30 and another region in the vicinity of the detachment region 30. For example, electrical current can pass between the fluid 170 and the detachment region 30. Fluids other than the fluid 170 from the fluid source 150 can also contribute to an electrical pathway. For example, blood from the body of the patient may mix with the fluid 170 and form a portion or the entirety of the pathway. According to some embodiments, for example as shown in FIG. 9, fluid flow 170 can be provided during electrolytic detachment of the implant 20 from the delivery wire 44. For example, an infusion of fluid from the fluid source 150 by the pump 162 can be provided via the lumen 124 of the delivery catheter 100 past the detachment region 30.

According to some embodiments, severance of the detachment zone 30 can be achieved by a variety of mechanisms. Separation along the detachment zone 30 can be achieved by electrolytic corrosion, mechanical release, chemical reactions, thermal activity, or combinations thereof. By any means, the result of the separation can include the complete separation of the implant 20 from at least a portion of the delivery wire 44.

According to some embodiments, for example as shown in FIG. 10, full separation along the detachment zone 30 results in the implant 20 being entirely separated from at least a portion of the delivery wire 44. The portions of the delivery wire 44 that were located on the implant side of the detachment zone 30 can be readily retracted into the hub 50 and/or the implant 20 as described herein. As a result, such portions (e.g., the distal region 42 of the delivery wire 44, the distal insulating layer 32, the proximal section 70, and/or the distal section 80) can be moved distally to be located entirely distal to the proximalmost terminal end of the implant 20 (e.g., the hub 50). Such portions can be retained securely within the implant. Thrombosis formation within the implant 20 (e.g., within the cavity 90) can further secure such portions within the implant 20. In the final configuration described above, the extent to which the delivery wire 44 protrudes proximally of the implant 20 is reduced when compared to a delivery wire that is fixed relative to an implant. Once the protruding end of the delivery wire 44 is retracted within the implant 20, the remaining outer periphery of the implant 20 can be atraumatic. The reduction or elimination of a protrusion beneficially reduces a risk that such a protruding end would damage surrounding tissue.

Upon detachment, the delivery wire 44 and the delivery catheter 100 can be retracted away from the target site and out of the patient, leaving the implant 20 at the target site.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplifying approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An implant comprising:
   a proximal hub defining a lumen;
   an expandable portion extending distally from the proximal hub, the expandable portion configured to define an open volume in an uncompressed state, the open volume in fluid communication with the lumen; and
   an expansion member having a distal end portion coupled to the proximal hub and a proximal end portion coupled to a distal region of a delivery wire, the expansion member being biased to contract from a non-relaxed state toward a relaxed state and thereby move the distal region of the delivery wire distally toward the distal end portion of the expansion member, wherein the expansion member does not extend to a distal end of the implant, and
   wherein at least a portion of the delivery wire is disposed within the lumen.

2. The implant of claim 1, wherein the expansion member comprises a spring.

3. The implant of claim 2, wherein the spring comprises a tension spring.

4. The implant of claim 1, wherein the delivery wire comprises an electrolytically corrodible section proximal to the distal region.

5. The implant of claim 1, wherein the delivery wire comprises a detachment zone proximal to the distal region.

6. The implant of claim 5, further comprising a coating that electrically insulates the detachment zone of the delivery wire from the proximal hub.

7. The implant of claim 1, wherein the expansion member includes one or more elastic properties.

8. The implant of claim 1, wherein the expandable portion includes a braid ball, vasoocclusive coil, stent, filter, flow diverter, or a combination thereof.

9. A delivery system comprising:
   an implant having a proximal hub defining a lumen and an expandable portion extending distally from the proximal hub, the expandable portion configured to define an open volume in an uncompressed state, the open volume in fluid communication with the lumen;
   a delivery wire extending at least partially through the lumen, the delivery wire having a distal region and a detachment zone proximal to the distal region;
   an expansion member having a distal end portion coupled to the proximal hub and a proximal end portion coupled to the delivery wire distal region, the expansion member being biased to contract from a non-relaxed state toward a relaxed state and thereby move the distal region of the delivery wire distally toward the distal end portion of the expansion member, wherein the expansion member does not extend to a distal end of the implant; and
   a catheter, wherein at least a section of the delivery wire is within the catheter.

10. The delivery system of claim 9, wherein the expansion member comprises a spring.

11. The delivery system of claim 9, wherein the expansion member comprises a tension spring.

12. The delivery system of claim 9, wherein at least a portion of the delivery wire extends entirely through the lumen.

13. The delivery system of claim 9, wherein the detachment zone comprises an electrolytically corrodible section.

14. The delivery system of claim 9, wherein a distal cross-sectional dimension of the distal region is greater than a proximal cross-sectional dimension of the detachment zone.

15. The delivery system of claim 9, further comprising a coating layer that electrically insulates the detachment zone of the delivery wire from the proximal hub.

16. The delivery system of claim 9, wherein the expansion member includes one or more elastic properties.

17. The delivery system of claim 9, wherein the expandable portion includes a braid ball, vasooclusive coil, stent, filter, flow diverter, or a combination thereof.

* * * * *